United States Patent [19]

Wilk

[11] Patent Number: 5,368,015

[45] Date of Patent: * Nov. 29, 1994

[54] AUTOMATED SURGICAL SYSTEM AND APPARATUS

[76] Inventor: Peter J. Wilk, 185 West End Ave., New York, N.Y. 10023

[ * ] Notice: The portion of the term of this patent subsequent to Jun. 8, 2010 has been disclaimed.

[21] Appl. No.: 73,355

[22] Filed: Jun. 7, 1993

Related U.S. Application Data

[63] Continuation-in-part of Ser. No. 670,720, Mar. 18, 1991, Pat. No. 5,217,003, and a continuation-in-part of Ser. No. 682,002, Apr. 8, 1991, Pat. No. 5,217,453.

[51] Int. Cl.$^5$ .............................. A61B 1/00; A61B 1/06
[52] U.S. Cl. ............................................ 128/4; 128/6; 128/903
[58] Field of Search ............... 128/4, 6, 903; 606/7, 606/159, 180; 604/95, 159

[56] References Cited

U.S. PATENT DOCUMENTS

| | | | |
|---|---|---|---|
| 3,834,392 | 9/1974 | Lampman et al. | 128/4 X |
| 4,343,300 | 8/1982 | Hattori | 128/6 |
| 4,499,895 | 2/1985 | Takagama | 128/6 |
| 4,572,198 | 2/1986 | Codrington | |
| 4,573,452 | 3/1986 | Greenberg | |
| 4,601,705 | 7/1986 | McCoy | |
| 4,621,618 | 11/1986 | Omagari | 128/6 |
| 4,633,304 | 12/1986 | Nagasaki | |
| 4,672,963 | 6/1987 | Barken | |
| 4,758,222 | 7/1988 | McCoy | 128/6 X |
| 4,785,806 | 11/1988 | Decklebaum | |
| 4,788,975 | 12/1988 | Shturman et al. | |
| 4,790,813 | 12/1988 | Keasey | |
| 4,791,934 | 12/1988 | Brunnett | 128/4 |
| 4,875,897 | 10/1989 | Lee | |
| 4,887,605 | 12/1989 | Angelsen et al. | |
| 4,974,607 | 12/1990 | Miwa | |
| 4,996,975 | 3/1991 | Nakamura | 128/4 X |
| 5,078,714 | 1/1992 | Katims | |
| 5,104,392 | 4/1992 | Kittrell et al. | |
| 5,125,888 | 6/1992 | Howard et al. | |
| 5,203,781 | 4/1993 | Bonati et al. | 128/4 X |
| 5,217,001 | 6/1993 | Nakao et al. | 128/4 |
| 5,217,003 | 6/1993 | Wilk | 128/4 |
| 5,217,453 | 6/1993 | Wilk | 606/7 |
| 5,228,429 | 7/1993 | Hatano | 128/4 |
| 5,259,365 | 11/1993 | Nishikori et al. | 128/4 |

FOREIGN PATENT DOCUMENTS

| | | |
|---|---|---|
| 0079524 | 5/1983 | European Pat. Off. |
| 0467459 | 11/1992 | European Pat. Off. |
| 3431022 | 3/1985 | Germany |
| 9101687 | 2/1991 | WIPO |

*Primary Examiner*—Gene Mancene
*Assistant Examiner*—Nicholas D. Lucchesi
*Attorney, Agent, or Firm*—R. Neil Sudol; Henry D. Coleman

[57] ABSTRACT

A surgical system comprises an endoscopic instrument, a camera on the endoscopic instrument for obtaining video images of internal body tissues inside a patient's body via the endoscopic instrument, and a transmitter operatively connected to the camera for transmitting, over a telecommunications link to a remote location beyond a range of direct visual contact with the patient's body, a video signal encoding the video image. A receiver is provided for receiving actuator control signals from the remote location via the telecommunications link. The receiver feeds the signals to a robot actuator mechanism for controlling that mechanism to operate a surgical instrument insertable into the patient's body.

20 Claims, 8 Drawing Sheets

AUTOMATED SURGICAL SYSTEM AND APPARATUS

CROSS-REFERENCE TO RELATED APPLICATIONS

This application is a continuation-in-part of application Ser. No. 670,720 filed Mar. 18, 1991, now U.S. Pat. No. 5,217,003. This application is also a continuation-in-part of application Ser. No. 682,002 filed Apr. 8, 1991, now U.S. Pat. No. 5,217,453.

BACKGROUND OF THE INVENTION

This invention relates to a surgical system and a related method. More particularly, this invention relates to an endoscopic or laparoscopic surgical method and apparatus.

The advantages of laparoscopic and endoscopic surgical methods have become increasingly apparent to surgeons and to society at large. Such surgical techniques are minimally invasive, require less operating time, and reduce trauma and convalescence time required after surgery is completed. In general, noninvasive surgery using laparoscopic and endoscopic techniques will be used more and more frequently to reduce hospital and surgical costs.

In endoscopic and laparoscopic surgery, the surgeon is provided with visual information through optical fibers extending through the endoscope or laparoscope. Sometimes, the visual information is provided to the surgeon and other operating room personnel via video monitors which show images obtained by small video cameras (charge coupled devices) at the distal ends of the endoscopes or laparoscopes. Although this video information may be transmitted to other rooms in the hospital or other institutional clinical setting, the surgeon is always present in the operating room to manipulate the surgical instruments and thereby perform the surgical operation in response to the video images on a monitor.

The use of video images provides an opportunity for further reductions in the expense and time required for surgery.

OBJECTS OF THE INVENTION

An object of the present invention is to provide a method and apparatus which facilitates the performance of operations by surgeons from all over the world.

A related object of the present invention is to provide a method and/or associated apparatus for enabling a surgeon in one location to perform operations in different cities or different countries without the surgeon having to move from one room.

Another object of the present invention is to provide a method and/or associated apparatus which facilitates the performance of surgery, thereby reducing fatigue and incrementing efficiencies of surgeons.

An object of the present invention is to provide a method and apparatus which reduces costs of performing surgery such as endoscopic and laparoscopic and angioscopic surgery.

SUMMARY OF THE INVENTION

A surgical method comprises, in accordance with the present invention, the steps of (a) providing an endoscopic instrument assembly with a flexible insertion member, the endoscopic instrument assembly having a plurality of biopsy channels extending parallel to the insertion member, (b) also providing a plurality of flexible endoscopic tools having distal end portions, (c) inserting the insertion member into a patient's body, (d) obtaining a video image of internal body tissues inside the patient's body via the endoscopic instrument assembly, (e) transmitting, over an electromagnetic signaling link, a video signal encoding the video image to a remote location beyond a range of direct manual contact with the patient's body and the endoscopic instrument, (f) receiving actuator control signals from the remote location via the electromagnetic signaling link, (g) automatically inserting distal end portions of the tools into the patient's body via respective ones of the biopsy channels in response to the received actuator control signals, and (h) automatically operating the tools in response to the received actuator control signals to effect a surgical operation on the internal body tissues.

Where the endoscopic instrument assembly includes a pair of image transmission guides and the video signal includes stereoscopic information from the image transmission guides, the method further comprises the step of providing stereoscopic visual information to a surgeon at the remote location.

The stereoscopic visual information may be provided at the remote location by generating a single video image having staggered image components of different colors, filters over different eyes of a viewer serving to select between the staggered image components.

Alternatively, the stereoscopic visual information may be provided at the remote location by providing two video monitors attached to one another for mounting to a person's head and, generating on the monitors, two video images having staggered or parallax-shifted image components.

According to another feature of the present invention, the method further comprises the step of automatically bending the distal end portions of the tools the tools in response to the received actuator control signals.

A surgical system comprises, in accordance with the present invention, an endoscopic instrument, camera componentry attached to the endoscopic instrument for obtaining video images of internal body tissues inside a patient's body via the endoscopic instrument, and a transmitter operatively connected to the camera componentry for transmitting, over an electromagnetic signaling link to a remote location beyond a range of direct manual contact with the patient's body and the endoscopic instrument, a video signal encoding the video image. A receiver is provided for receiving actuator control signals from the remote location via the electromagnetic signaling link. A surgical instrument insertable into the patient's body and movable relative to the patient's body and the endoscopic instrument has a replaceable operative tip and is operatively connected to a robotic actuator which actuates the surgical instrument in response to the actuator control signals received by the receiver from the remote location. A robotic selector is operatively connected to the surgical instrument and the receiver for removing the operative tip and replacing the operative tip with a different operating tip in response to the actuator control signals received by the receiver from the remote location.

According to another feature of the present invention, means are provided for automatically operating the endoscopic instrument in response to additional signals received by the receiver from the remote location via the telecommunications link.

The robotic actuator may be a separate mechanism from the robotic selector. The two cooperate with one another, however, in an instrument tip replacement procedure. To enable the remote user (surgeon) to control the replcament procedure, additional camera componentry is disposed permanently outside the patient and is operatively connected to the transmitter for transmitting to the remote location a video image of a tool array disposed proximately to the patient.

According to a further feature of the present invention, the camera componentry includes means for obtaining stereoscopic images of the internal body tissues.

A surgical system comprises, in accordance with another conceptualization of the present invention, an endoscopic instrument, camera componentry connected to the endoscopic instrument for obtaining stereoscopic video images of internal body tissues inside a patient's body via the endoscopic instrument, and a transmitter operatively connected to the camera componentry for transmitting, over an electromagnetic signaling link to a remote location beyond a range of direct manual contact with the patient's body and the endoscopic instrument, a video signal encoding the video images. A receiver is provided for receiving actuator control signals from the remote location via the electromagnetic signaling link, while a surgical instrument is insertable into the patient's body and movable relative to the patient's body and the endoscopic instrument. A robotic actuator is operatively connected to the surgical instrument and the receiver for actuating the surgical instrument in response to the actuator control signals received by the receiver from the remote location.

According to an additional feature of this conceptualization of the present invention, the camera componentry includes a first video camera and a second video camera. A first optical input is provided for receiving light reflected from the internal body tissues of the patient during a surgical procedure, the first optical input being operatively connected to the first camera for focusing a first image of the internal body tissues on photoreceptive componentry of the first camera. A second optical input receives light reflected from the internal body tissues during the surgical procedure and is operatively connected to the second camera for focusing a second image of the internal body tissues on photoreceptive componentry of the second camera. A spacer element is operatively connected to the first and the second optical inputs for maintaining the inputs spaced from one another inside the patient during the surgical procedure.

According to a more particular embodiment of the present invention, the cmaera assembly incpudes an elongate rigid member provided at a distal end with a pair of prongs. The spacer includes the prongs. The first optical input and the second optical input are disposed at distal ends of respective ones of the prongs, while shifting componentry is operatively connected to the prongs for shifting the prongs away from one another upon an insertion of the elongate rigid member through a laparoscopic trocar sleeve traversing a skin surface of a patient.

According to an alternative particular embodiment of the present invention, the spacer includes a laparoscopic trocar sleeve having two instrument insertion channels oriented at an acute angle relative to one another. The optical inputs are disposed at distal ends of respective elongate rods which are inserted through respective instrument insertion channels of the trocar sleeve.

According to a further alternative particular embodimetn of the present invention, the camera componentry comprises a first elongate rigid member, the spacer including a second elongate rigid member pivotably connected to a distal end of the first elongate rigid member. The optical inputs are disposed at opposite ends of the second elongate Member. The second elongate rigid member is pivoted relative to the first elongate rigid member from an insertion configuration parallel to the first elongate rigid member to a use configuration at a predetermined angle with respect to the first elongate rigid member.

A robotic surgery system and methodology in accordance with the present invention facilitates the performance of surgery by having the surgeon spaced from the patient. The surgeon may be in another room, or in another city.

DETAILED DESCRIPTION

Figure 1:
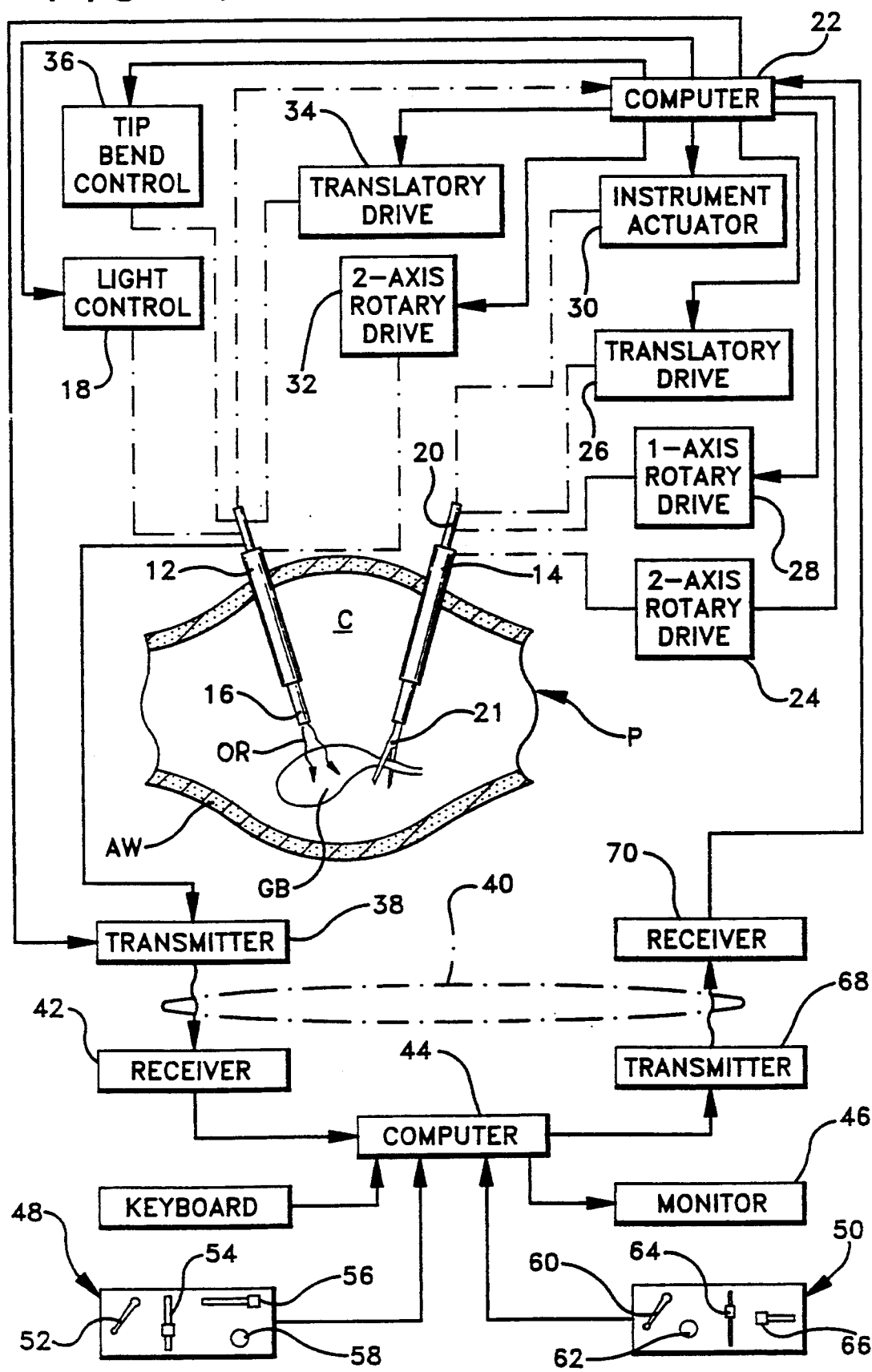
FIG. 1 is a diagram of a remotely controlled operating system, in accordance with the present invention, for performing laparoscopic surgery.

As illustrated in FIG. 1, a patient P undergoing laparoscopic surgery, for example, removal of a gall bladder GB, has an internal body cavity C pressurized with air to distend the abdominal wall AW. The abdominal wall is pierced with a trocar (not shown) and a plurality of hollow tubes 12 and 14 are inserted through the abdominal wall to provide passage for the operating instruments. One such instrument is an endoscopic type device, namely, a laparoscope 16 which includes an optical fiber (not illustrated) for delivering optical radiation OR from a light source or control component 18 to the surgical site. Another instrument takes the form of a forceps instrument shaft 20 or other device for manipulating and/or severing internal body tissues such as gall bladder GW.

Forceps instrument 20 includes a pair of forceps jaws 21 whose position inside body cavity C is controlled by a computer 22 via a two-axis rotary drive 24 and a translatory drive 26. Rotary drive 24 is operatively connected to tube 14 for pivoting the tube at its point of penetration through abdominal wall about two axes of rotation. In response to signals from computer 22, translatory drive 26 slides forceps instrument 20 longitudinally through tube 14.

The orientation of forceps jaws 21 is controlled by computer 22 via a one- or two-axis rotary drive 28, while forceps jaws 21 are alternately opened and closed by an actuation mechanism 30 in response to control signals from computer 22.

The position of a distal tip of laparoscope 16 inside body cavity C is controlled by computer 22 via a two-axis rotary drive 32 mechanically linked to tube 14 and a translatory drive 34 operatively coupled with laparoscope 16. Translatory drive 34 varies the degree of insertion of laparoscope 16 through tube 12, while rotary drive 32 swings tube 12 about two axes of rotation.

The intensity and/or the hue of optical radiation OR is controlled by computer 22 via light source or control component 18. In addition, in the event that laparoscope 16 is flexible, the curvature of the distal end portion of the laparoscope is modifiable by computer 22 via a bend control component 36.

Laparoscope 16 incorporates a charge coupled device (not illustrated) for converting optical incoming optical radiation, reflected from internal body tissues inside cavity C, to a video signal. That video signal, encoding a video image, is transmitted from laparoscope 16 to a transmitter 38 and optionally to computer 22.

Transmitter 38 in turn transmits the video signal over a telecommunications link 40 to a remote receiver 42 which relays the video signal to another computer 44. Computer 44 uses the incoming video signal to display on a monitor 46 an image of the internal body tissues of patient P.

Connected to computer 44 are at least two sets of input devices 48 and 50 operated by a surgeon to remotely control a surgical procedure. More specifically, input device 48 includes a joy stick 52 for controlling the operation of rotary drive 32, a slide switch 54 for controlling the operation of translatory drive 34, another slide switch 56 for controlling light source or control component 18 to modify light intensity, and a dial or knob 58 for controlling bend control component 36 to change the angle of inclination of the distal end portion of laparoscope 16.

Input device 50 includes a joy stick 60 for controlling the operation of rotary drive 24, a dial or knob 62 for controlling rotary drive 28, a slide switch 64 for controlling translatory drive 26, and another slide switch 66 for controlling instrument actuator 30.

Signals from input devices 48 and 50 are encoded by computer 44 and sent to computer 22 via a transmitter 68, telecommunications link 40, and a receiver 70. Computer 22 then uses the incoming signals to provide control signals to the various drives and other components at the site of the surgery.

It is to be understood, of course, that surgeons and other personnel are present in the operating room at the time of surgery to oversee and supervise the proper operation of the equipment. These personnel may communicate with the remote surgeon via computers 22 and 44 and telecommunications link 40 and/or through other telecommunications linkages such as the telephone network. To facilitate local supervision, computer 22 is connected to a local monitor (not shown) for displaying the video images garnished by laparoscope 16 and, for example, for displaying alphanumeric codes indicating the positions and operating statuses of the instruments, e.g., light source or control component 18 and forceps instrument 20. Such information may also be transmitted by computer 22 to computer 44 over transmitter 38, link 40 and receiver 42 and displayed on monitor 46. Other parameters regarding the condition of patient P, such as temperature, heart rate, oxygen consumption, brain wave activity, and blood sugar level, may also be automatically sensed, encoded and transmitted to remote computer 44 for providing the lead surgeon in real time with all information necessary for performing the surgery successfully.

Figure 2:
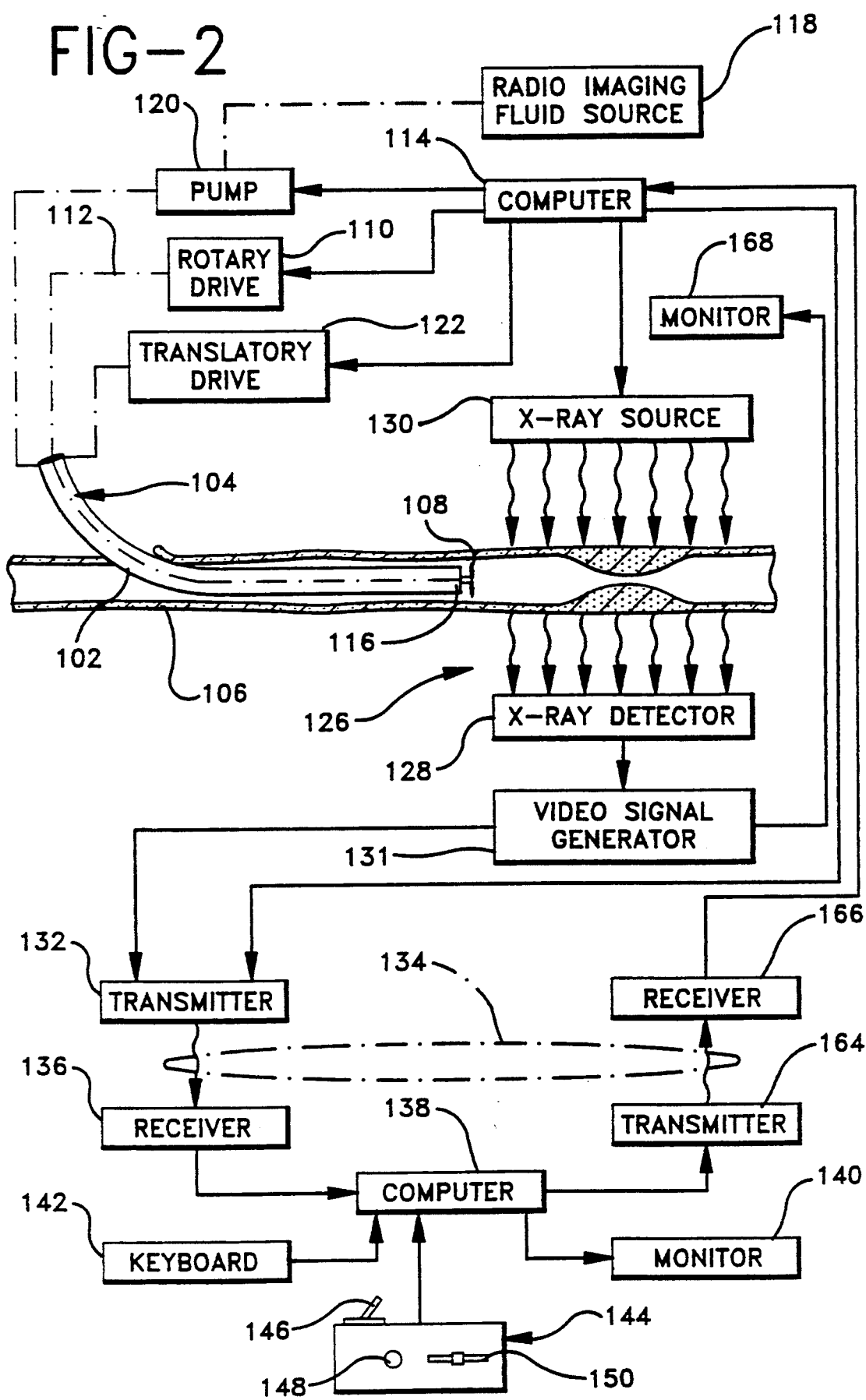
FIG. 2 is a diagram of another remotely controlled system for performing angioplastic surgery.

As illustrated in FIG. 2, a tubular member 102 of an angioplastic operating instrument 104 is inserted into a blood vessel 106 of a patient. At a distal end, instrument 104 includes a rotary blade 108 operatively linked to a drive 110 via a transmission member 112. Rotary drive 110 is operated or energized under the control of a computer 114.

At its distal end, instrument 104 is further provided with an opening 116 for injecting into vessel 106 a radiographic or radio-imaging fluid from a source 118. The injection operation is implemented by a pump 120 in response to actuating signals from computer 114.

Computer 114 controls the degree that tubular member 102 is inserted into vessel 106 by actuating a translatory drive 122 operative coupled to the tubular member.

The location of a blockage 124 inside vessel 106 is detectable via an electromagnetic imaging device 126 exemplarily taking the form of an X-ray detector 128 receiving X-rays from a source 130 via that part of the patient including vessel 106 and blockage 124. Blockage 124 is highlighted through the injection of the radio-imaging fluid from source 118. Alternatively, the radio-imaging fluid may be radioactive, electromagnetic imaging device 126 taking the form of a fluoroscope.

Upon the insertion of tubular member 102 into vessel 106, electrical signals encoding video images of structure inside vessel 106, such as blockage 124, are produced by a signal generator 131 connected at an output of X-ray detector 128. The video signals are sent via a transmitter 132 and a telecommunications link 134 to a remote receiver 136 which relays the video signal to a computer 138. Computer 138 uses the incoming video signal to display on a monitor 140 an image of structure internal to vessel 106. Transmitter 132, telecommunications link 134 and receiver 136 are also used to transmit data from local computer 114 to remote computer 138.

A keyboard 142 and an optional switchboard or console 144 are connected to computer 138 for enabling a surgeon at a remote location to control the operation of instrument 104. More particularly, console 144 includes a toggle switch 146 for controlling the operation of rotary drive 110, a knob 148 for controlling the operation of pump 120, and a slide switch 150 for determining the distance that tubular member 102 is inserted in vessel 106. The remote surgeon manipulates switches 146 and 150 and knob 148 in response to video images on monitor 140. Those images are themselves changed by the surgeon by shifting tubular member 102 further along vessel 106 and by periodically injecting radio-imaging fluid into the vessel from source 118.

Figure 3:
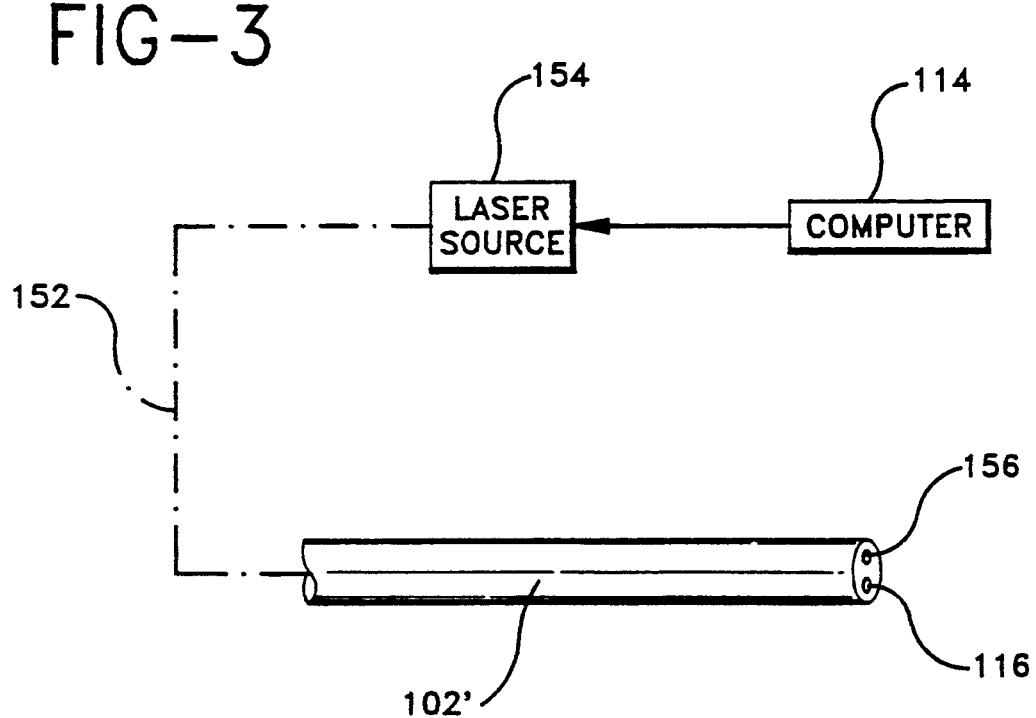
FIG. 3 is a diagram of a modified portion of the system of FIG. 2.
Figure 4:
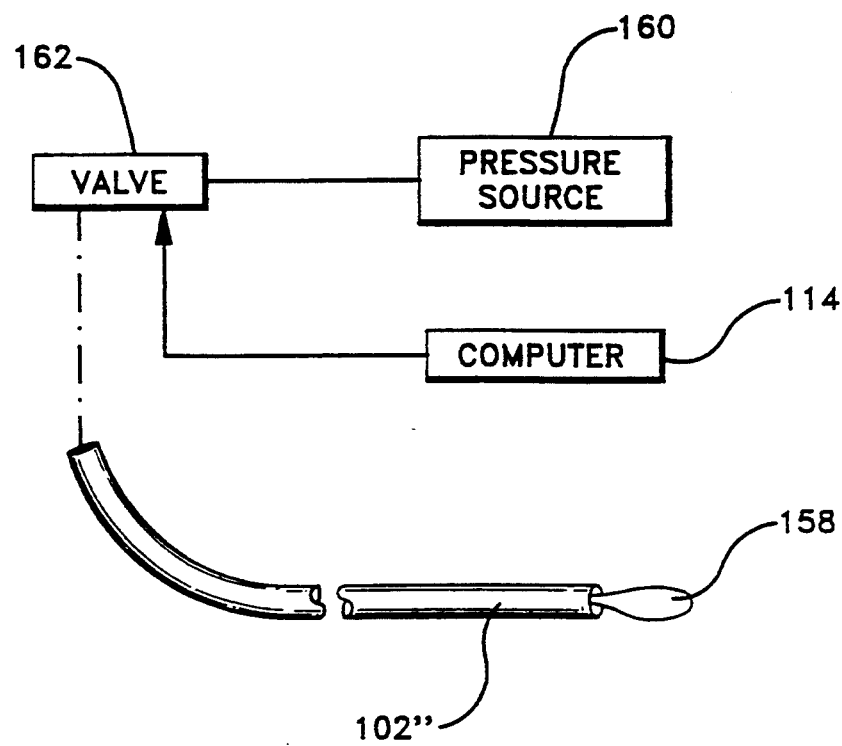
FIG. 4 is a diagram of a portion of the system of FIG. 2, modified in another way.

FIG. 3 illustrates a modification of the system of FIG. 2 wherein the surgical tool in a tubular angioplastic surgical member 102' takes the form of an optical fiber 152 for guiding a laser beam from a source 154 to an exit 156 at the distal end of the tubular member. FIG. 4 depicts an alternative modification wherein the blockage removal tool takes the form of an inflatable balloon or bladder 158 disposed at a distal end of an angioplastic surgical member 102''. Bladder 158 is expanded by pressure released from a pressurized gas source 160 by opening a valve 162 in response to signals from computer 114. Of course, computer 114 operates in response to signals from computer 138.

As discussed hereinabove with reference to FIG. 1, it is understood that surgeons and other personnel are present in the operating room at the time of surgery to oversee and supervise the proper operation of the equipment. These personnel may communicate with the remote surgeon via computers 114 and 138 and transmitters 132 and 164, receivers 136 and 166, and telecommunications link 134 and/or through other telecommunications linkages such as the telephone network. To facilitate local supervision, computer 114 is connected to a local monitor 168 for displaying the video images obtained by electromagnetic imaging device 126 and, for example, for displaying alphanumeric codes indicating the positions and operating statuses of the instruments. Such information may also be transmitted by computer 114 to computer 138 over transmitter 132, link 134 and receiver 136 and displayed on monitor 140. Other parameters regarding the condition of patient P, such as temperature, heart rate, oxygen consumption, brain wave activity, and blood sugar level, may also be automatically sensed, encoded and transmitted to remote computer 138 for providing the lead surgeon in real time with all information necessary for performing the surgery successfully.

Figure 5:
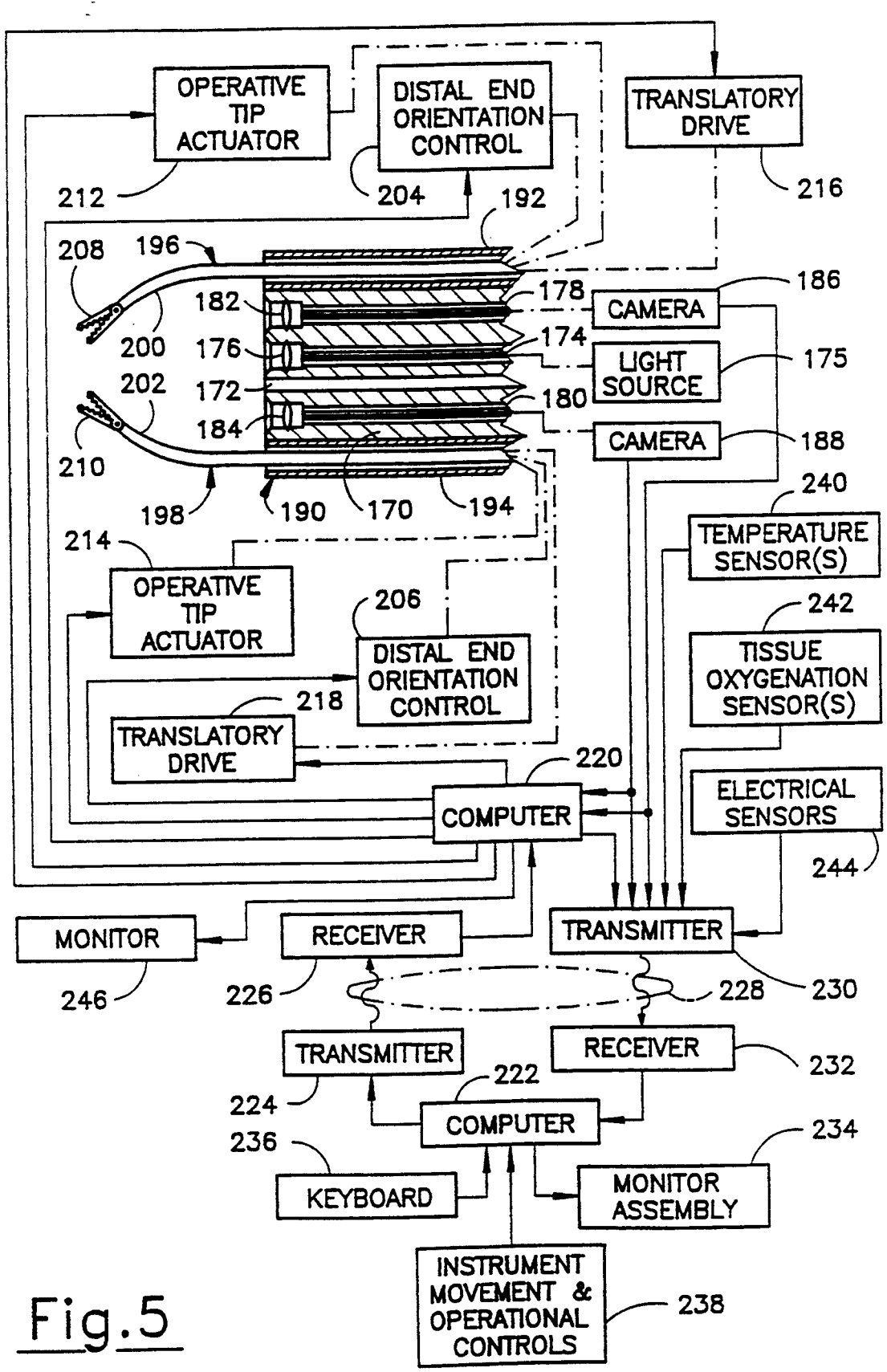
FIG. 5 is partially a schematic partial cross-sectional view of an endoscopic insertion member and partially a block diagram of a remotely controlled endoscopic surgical system, in accordance with the present invention.

As illustrated in FIG. 5, a remote-controllable endoscopic surgery system comprises an endoscope insertion member 170 having a biopsy channel 172 and a fiber optic illumination guide 174 extending from a light source 175 to a lens 176 at the distal end of insertion member 170. Insertion member 170 also has a pair of fiber optic image transmission guides 178 and 180 extending from focusing lenses 182 and 184 to respective cameras (e.g., charge coupled devices) 186 and 188 connected to the insertion member 170.

Endoscope insertion member 170 is surrounded by a sheath 190 having a plurality of expandable channels 192 and 194 for the insertion of respective flexible endoscopic instruments or tools 196 and 198. Each endoscopic instrument 196 and 198 has a bendable distal end portion 200 and 202 whose orientation is determined, e.g., via tension cables (not shown), by a respective distal orientation control 204 and 206. Each endoscopic instrument 196 and 198 has an operative tip 208 and 210, the operation of which is controlled by a respective actuator 212 and 214 operatively coupled to the respective endoscopic instrument. In addition, the linear position of each endoscopic instrument 196 and 198 relative to endoscopic insertion member 170 is modified by a respective translatory drive 216 and 218.

Sheath 190 may have a form as described and illustrated in U.S. Pat. No. 5,217,001 to Nakao and Wilk. The disclosure of that patent is hereby incorporated by reference herein.

The operation of orientation controls 204 and 206, actuators 212 and 214, and translatory drives 216 and 218 is controlled by a local computer 220 in response to signals received from a remote computer 222 via a remote wireless transmitter 224 and a local receiver 226 of an electromagnetic telecommunications link 228. Telecommunications link 228 also includes a local wireless transmitter 230 and a remote receiver 232. Local transmitter 230 is operatively connected to cameras 186 and 188 for receiving respective video signals therefrom, those signals encoding stereoscopic (staggered or parallax-shifted) images of essentially the same internal body tissues of a patient.

At the remote station occupied in part by computer 222 (which may in fact be in a room adjacent to the operating room), computer 222 is connected to a monitor assembly 234 which presents a stereoscopic image to a viewer. Monitor assembly 234 may comprise a single video monitor operated by computer 222 to show the staggered or parallax-shifted images of a stereoscopic picture in different colors. In a conventional step of the procedure, a surgeon at the remote station wears a pairs of glasses with lenses of different hues, whereby each eye is presented with a different image.

Remote computer 222 is also connected to a keyboard 236 and a console 238 for controlling linear movement, distal end bending, and tip operation of endoscopic instruments 196 and 198. Console 238 may be provided with rotary and slide controls as described hereinabove with reference to FIG. 1. Alterantively or additionally, console 238 may include one or more mouse actuators for determining the use of endoscopic instruments 196 and 198. The remote surgeon manipulates the controls (not shown) of console 238 in response to steroscopic video images on monitor assembly 234. Those images are themselves changed by the surgeon by shifting insertion member 170 further along a hollow organ or body cavity in which the distal end of insertion member 170 is disposed.

As further illustrated in FIG. 5, temperature sensors 240, tissue oxygenation sensors 242, and electrical brain activity detectors 244 are operatively connected to local transmitter 230 for transmitting to the surgeon at the remotely station instantaneous or real-time values of physiological parameters of the patient.

A monitor 246 is connected to local computer 220 for displaying images available to the remote surgeon via monitor assembly 234.

Figure 6:
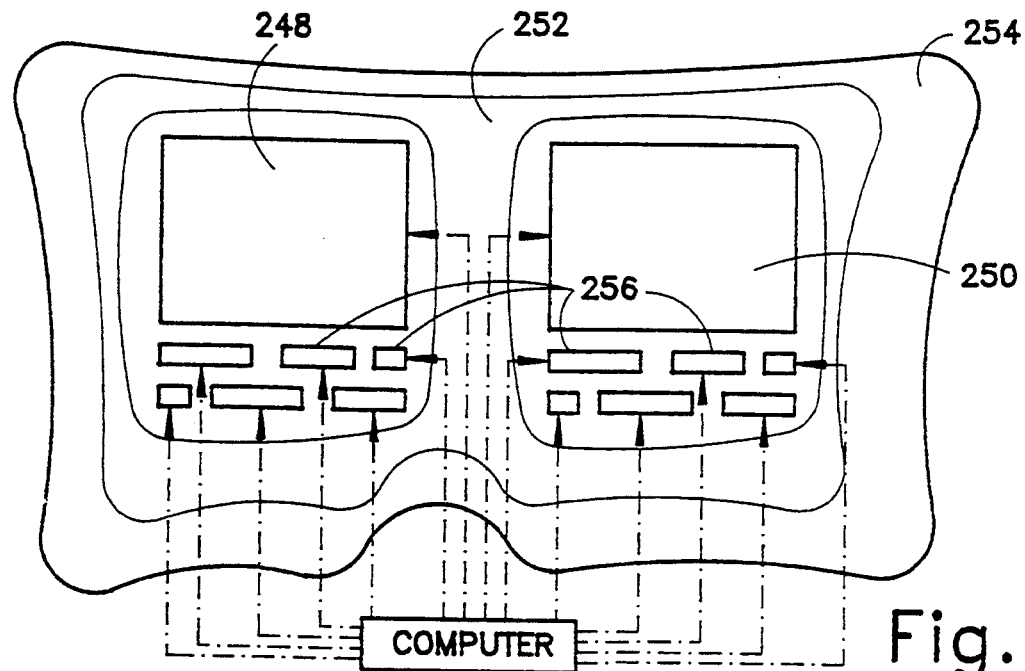
FIG. 6 is partially a schematic elevational view and partially a block diagram of a steroscopic monitor assembly in the system of FIG. 5.

As depicted in FIG. 6, two video images of a stereosopic picture may be presented via a pair pf video monitors 248 and 250 mounted to a frame 252 which is provided along its edges with an elastically deformable light seal 254 engageable with the different planes of a person's face. Also mounted to frame 252 are a plurality of digital (e.g., LCD) displays 256 for informing the user of sensed physiological parameters of the patient, as well as other conditions of a remotely controlled operation such as the degree of insertion of the endoscopic insertion member 170. To that end, insertion member 170 is provided with pressure and/or temperature sensors along its length for sensing which portions of the endoscope insertion member are inside the patient and which portions are in the ambient air.

Monitors 248 and 250 and displays 256 are operatively connected at inputs to remote computer 222.

Figures 7, 8:
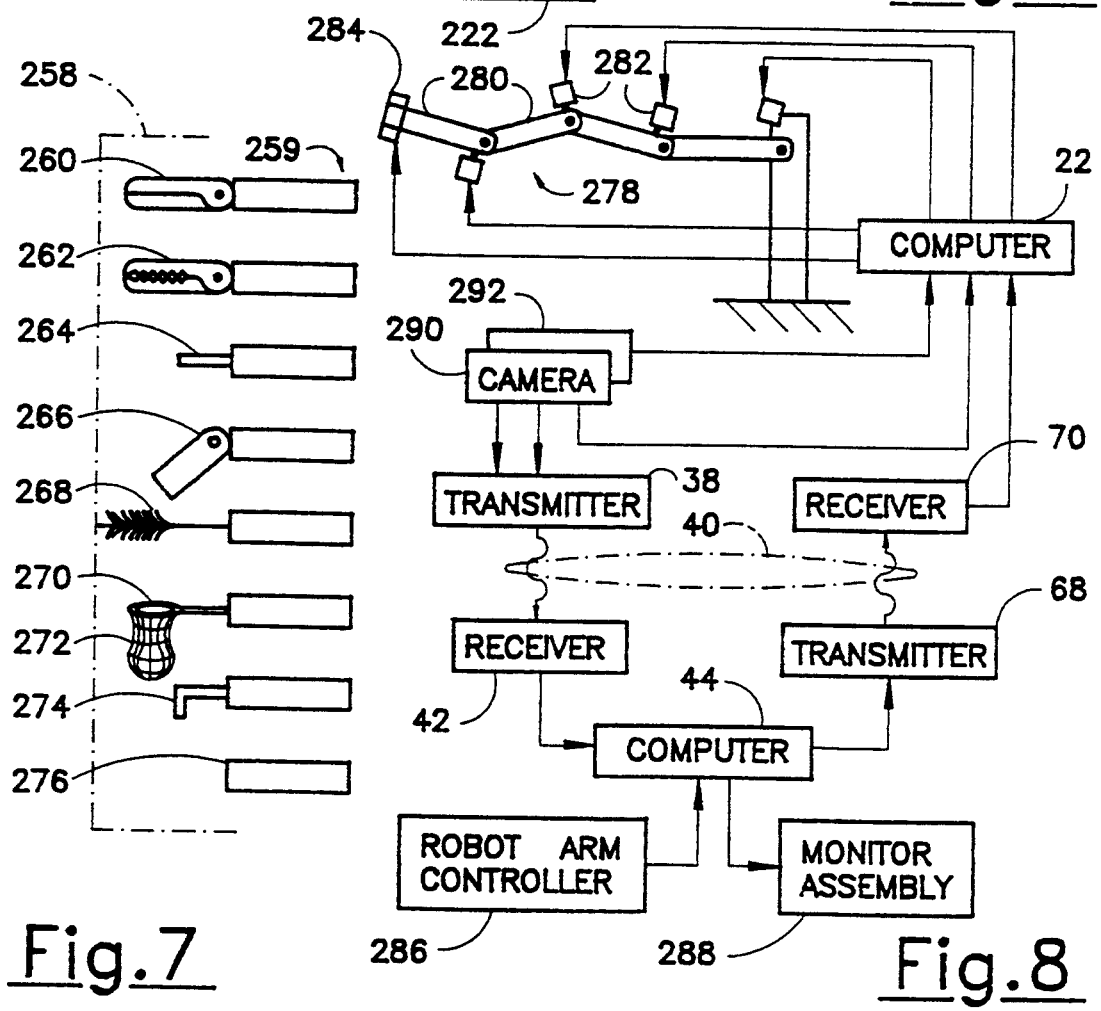
FIG. 7 is a diagram of a magazine or storage unit for a multiplicity of replaceable surgical operating tips for use in a system and an associated method in accordance with the present invention.
FIG. 8 is a block diagram of a modification to the system of FIG. 1, showing a robotic selector mechanism for replacing an operative tip of a laparoscopic instrument shown in FIG. 1.

As illustrated in FIG. 7, a schematically represented casing or shelving unit 258 carries, in predetermined locations marked by visually readable tabs (not shown), a plurality of alternatively utilizable laparoscopic instrument tips 259 including a scissors 260, a graspers 262, a laser fiber 264, a retractor 266, a brush 268, a snare 270 including a capture pocket 272, a cauterization hook 274 and an irrigation tube 276. Generally, it is contemplated that shelving unit 258 holds the laparoscopic instruments in a two dimensional array in preassigned locations.

The instrument tips 259 in shelving 258 are alternately utilizable in place of jaws 21 (FIG. 1). To that end, instrument shaft 20 (FIG. 1) and operative tips 259 are provided at a distal end and proximal ends, respectively, with interlocking elements for releasably securing selected operative tips 259 to the laparoscopic instrument shaft.

The different operative tips 259 may be secured and removed manually from the laparoscopic instrument shaft, by technical assistants in the operating room. Alternatively, a remote controlled robot selector assembly as schematically illustrated in FIG. 8 may be an integral part of the remote operating system of FIG. 1. The remote controlled robot selector assembly of FIG. 8 comprises robot arm 278 having a plurality of articulated arm segments 280 whose relative positions are changed by rotary motors 282 under the control of local computer 22. It is to be understood that virtually any numerically controlled robot assembly can be substituted for robot arm 278 and motors 282. For example, a pantograph (not shown) with a pivoted base can reach all of the instrument tips 259 in shelving 258. Under the control of signals from computer 22, which in turn acts in response to signals from remote computer 44, a clamp 284 (e.g., electromagnetic or hydraulic) at the distal or free end of robot arm 278 captures a desired operative tip and secures the tip to instrument shaft 20 (FIG. 1).

To control robot arm 278, the remote station is provided with a controller 286 connected to remote computer 44. A stereoscopic monitor assembly 288 may be connected to computer 44 for enabling a user at the remote station to obtain stereoscopic images from a pair of ganged cameras 290 and 292 at the local station. Cameras 290 and 292 remain outside the patient and enable the remote user to visually determine the locations of desired instrument tips, as well as the location of inserted trocar sleeve 14 for inserting instrument shaft 20 after a new tip has been connected thereto under remote control.

Monitor assembly 288 may take the form described hereinabove with reference to FIG. 6. To obtain stereoscopic images of internal body tissues during a laparoscopic operation, the stereoscopic laparoscopic componentry of FIGS. 9–13 may be used.

To replace an operative tip (e.g., jaws 21 in FIG. 1) with another operatire tip 259 from storage magazine or shelving 258, the remote user opetranslatory drive 26 (FIG. 1) to remove instrument shaft 20 from trocar sleeve 14. Robotic selector arm 278 is then operated to place clamp 284 in proximity to forceps jaws 21. Clamp 284 is operated to remove jaws 21 from shaft 20. The attachment of a replacement tip is achieved by essentially reversing the steps.

Figure 9:
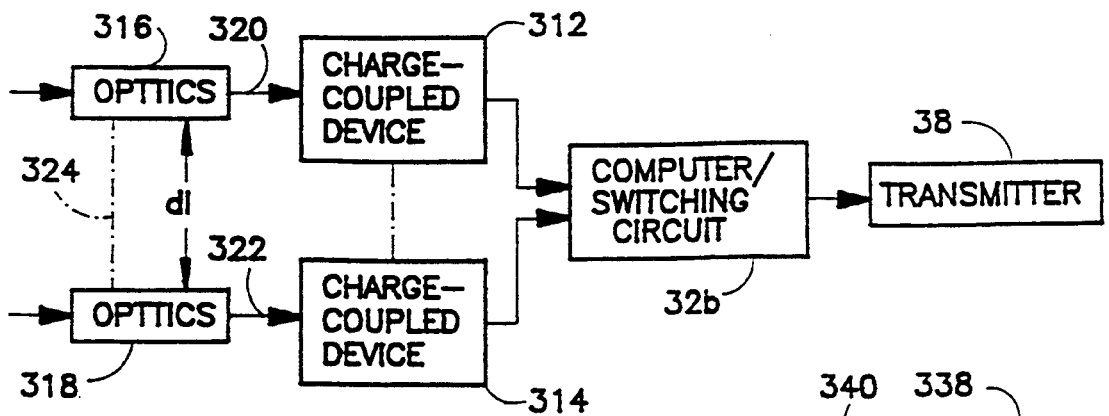
FIG. 9 is a block diagram of a stereoscopic laparoscope assembly utilizable in the robotic surgery system of FIG. 1.

As illustrated in FIG. 9, a stereoscopic laparoscope system comprises two video cameras 312 and 314 in the form of charge-coupled devices, and two optical input elements 316 and 318 such as lenses. Optical input elements 316 and 318 receive light reflected from an internal organ of a patient during a laparoscopic surgical procedure and transmit the images, e.g., directly or via optical fiber bundles 320 and 322, to photosensitive surfaces of cameras 312 and 314. Optical input elements 316 and 318 are operatively connected to cameras 312 and 314 so that respective images of the internal organ are focused on the photoreceptive componentry of the cameras.

As illustrated diagrammatically in FIG. 9, a spacer member 324 is operatively connected to optical input elements 316 and 318 for maintaining the optical input elements spaced from one another by a predetermined distance d1 inside the patient during the laparoscopic surgical procedure. Imaging circuitry in the form of a signal switching computer 326 is operatively connected at inputs to cameras 312 and 314 and at an output to transmitter 38 (FIG. 1).

Distance d1 between optical input elements 316 and 318 is preselected to represent an average interocular distance or the distance between the eyes of the operating surgeon(s). Distance d1 may be adjustable as described hereinafter with respective to particular embodiments of the system of FIG. 9.

Figure 10A:
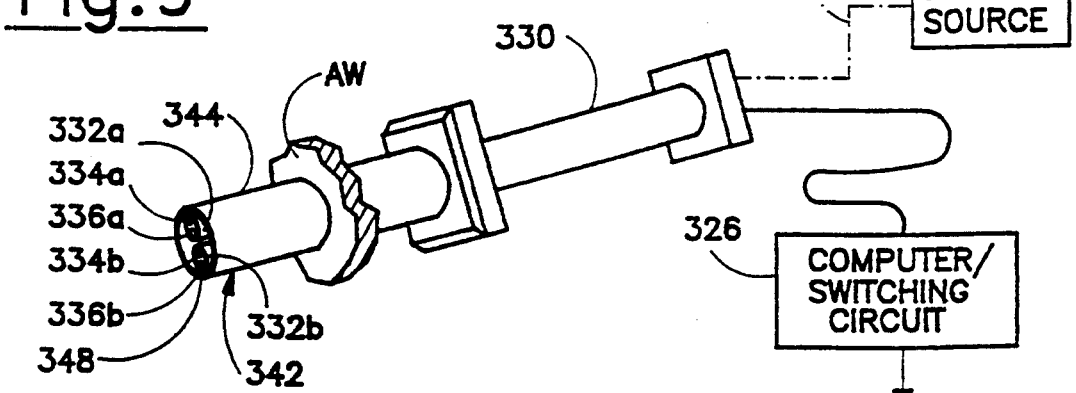
FIGS. 10A and 10B are partially block diagrams and partially schematic perspective views of a specific embodiment of the stereoscopic laparoscope assembly of FIG. 9, showing successive steps in the utilization of the system during a robotic laparoscopic surgical procedure in accordance with the present invention.

As illustrated in FIGS. 10A and 2B, the system of FIG. 9 may be realized by a laparoscopic instrument assembly including an elongate rigid member 30 which is bifurcated at a distal end into a pair of partially flexible prongs or branches 332a and 332b. Light-gathering lenses 334a and 334b which are specific realizations of optical elements 316 and 318 of FIG. 9 are disposed at distal ends of prongs 332a and 332b. Prongs 332a and 332b are additionally provided at their distal ends with illumination apertures 336a and 336b through which light is emitted to shine on internal tissues of a patient during a laparoscopic surgical procedure. The opticalfrequency electromagnetic radiation emitted through apertures 336a and 336b is generated by a light source 338 and transmitted via a bifurcated fiber-optic waveguide 340 to apertures 336a and 336b.

As illustrated in FIGS. 10A and 2B, rigid member 330 is inserted through a laparoscopic trocar sleeve 342 which has been inserted through a skin surface, particularly an abdominal wall AW, so that a distal end portion 344 of the trocar sleeve projects into an abdominal cavity of the patient. During insertion of rigid member 330 through trocar sleeve 342, which is depicted in FIG. 10A, prongs 332a and 332b are maintained in a parallel configuration in juxtaposition to one another by the trocar sleeve. Upon emergence of the prongs 332a and 332b from the distal end of trocar sleeve 342, the prongs are spread from the parallel insertion configuration to a separated use configuration shown in FIG. 10B.

The spreading of prongs 332a and 332b may be accomplished automatically by internal forces. To that end, prongs 332a and 332b are provided with respective actuation springs 346a and 346b which are biased to assume the configurations depicted in FIG. 10B. It is to be noted that the distance d1 (FIGS. 1 and 2B) between the distal tips of prongs 332a and 332b can be decreased from a maximum (FIG. 10B) by drawing member 330 in a proximal direction relative to trocar sleeve 342 so that the prongs are forced partially together by a camming action at a distal edge 348 of sleeve 342.

Prongs 332a and 332b perform the function of spacer member 324 illustrated schematically in FIG. 9. The spreading of prongs 332a and 332b upon an ejection thereof from trocar sleeve 342 may be implemented by an active actuator such as a tension cable assembly conventionally used in flexible endoscopes. Such an actuator assembly is considered equivalent to the inherent action of springs 346a and 346b.

Figure 10B:
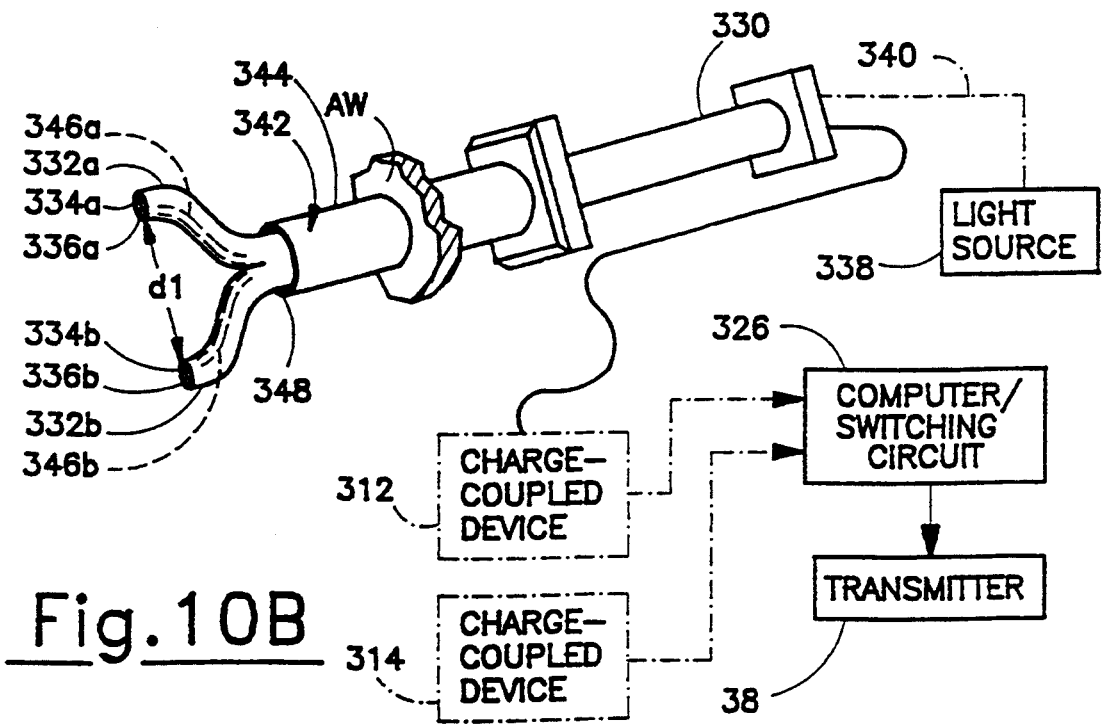

In the embodiment of FIGS. 10A and 10B, cameras 312 and 314 (FIG. 9) may be disposed at the distal ends of prongs 332a and 332b, proximally of light-gathering lenses 334a and 334b. Alternatively, cameras 312 and 314 are disposed at the proximal end of the instrument, outside rigid member 330. This embodiment is indicated by dot-dashed lines in FIG. 10B.

Figure 11:
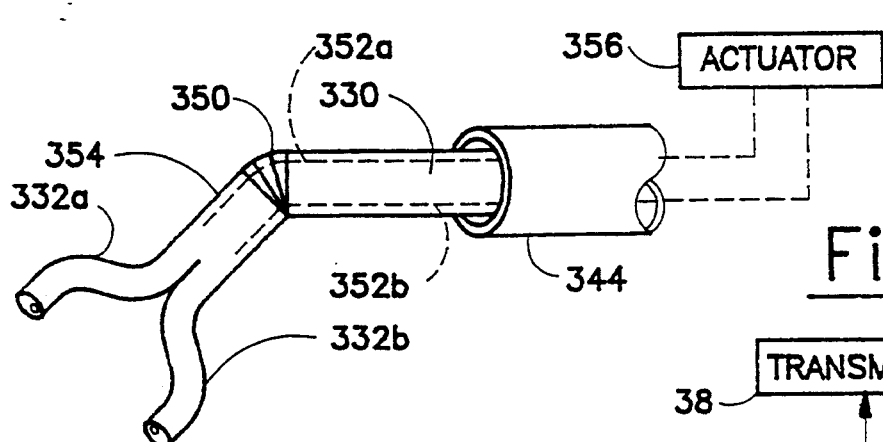
FIG. 11 is partially a block diagram and partially a partial schematic perspective view, similar to FIGS. 10A and 10B, showing a modification of the embodiment of FIGS. 10A and 10B.

As illustrated in FIG. 11, rigid member 330 may be provided with an articulation or joint 350, whereby prongs 332a and 332b, upon spreading thereof, may be turned to view different parts of the abdominal cavity of the patient. Tension cables 352a and 352b are connected at one end to a distal end portion 354 of rigid member 330 and at an opposite end to an actuator 356.

Figure 12A:
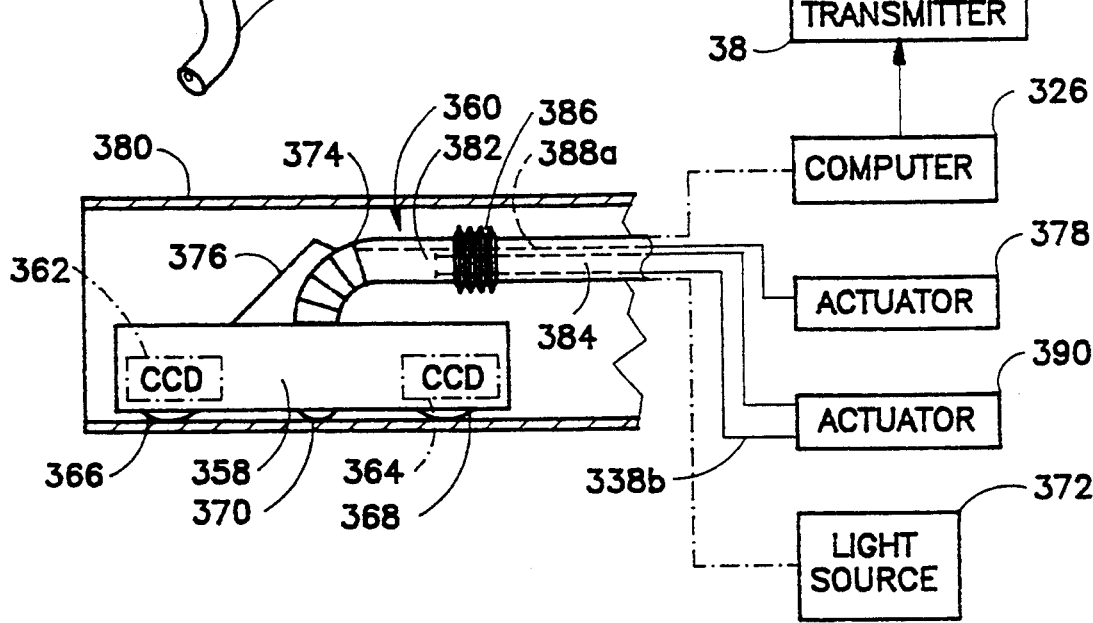
FIG. 12A is partially a block diagram and partially a schematic side elevational view of another specific embodiment of the stereoscopic laparoscope assembly of FIG. 9, showing a laparoscopic instrument in a folded configuration during insertion thereof through a sectioned trocar sleeve during a robotic laparoscopic procedure in accordance with the present invention.
Figure 12B:
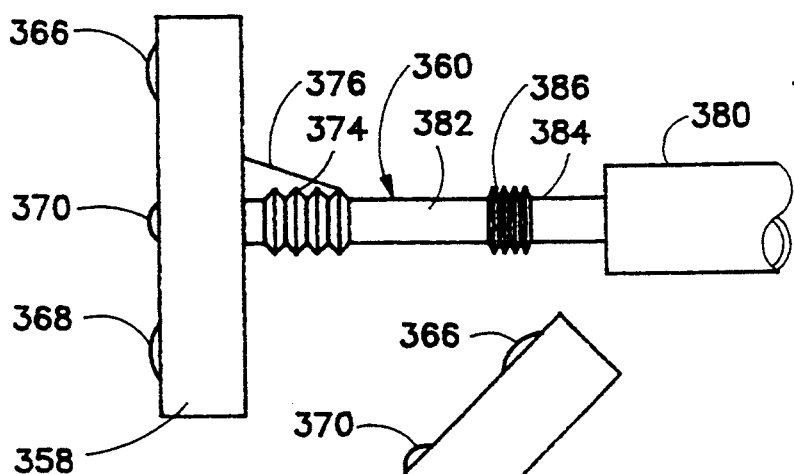
FIGS. 12B–12D are schematic side elevational views similar to FIG. 12A, showing the instrument of FIG. 12A in different use configurations relative to the trocar sleeve.

As shown in FIG. 12A, another laparoscopic instrument assembly for realizing the system of FIG. 9 includes an elongate rigid member or bar 358 pivotably connected to a distal end of another elongate rigid member 360. Charge-coupled devices 362 and 364 corresponding to cameras 312 and 314 (FIG. 9) are carried at opposite ends of bar 358. In addition, optical input elements in the form of lenses 366 and 368 are disposed at the opposite ends of bar 358 in juxtaposition to devices 362 and 364. Another lens 370, for emitting illuminating radiation generated by a light source 372, is disposed midway along bar 358.

Bar 358 is pivotably connected to a distal end of elongate rigid member 360 via a pivoting joint or articulation 374. A tensile element 376 is connected to bar 358 and extends through member 360 to an actuator 378 (such as a pull-ring) at the proximal end of member 360. Upon a pushing of member 360 in a distal direction through a laparoscopic trocar sleeve 380 so that bar 358 is ejected from the sleeve, tensile element 376 is pulled in the proximal direction relative to member 360, thereby pivoting bar 358 from a parallel configuration (FIG. 312A) to a position at a right angle with respect to member 360 (FIG. 10B). Lenses 366 and 368 are spaced a distance d1 (FIG. 9) from one another along bar 358 so that an image shown on monitor assembly 46 (FIG. 1) approximates or recreates human stereoscopic vision.

Figure 12C:
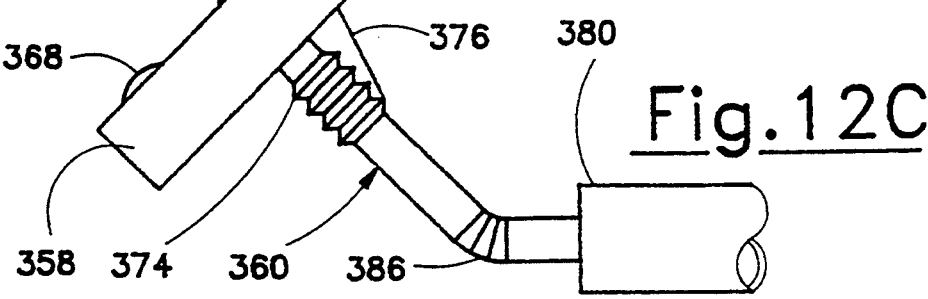
Figure 12D:
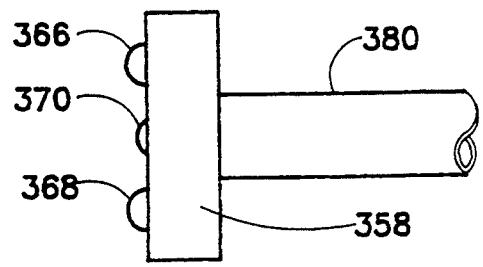

As shown in FIG. 12C, a distal end segment 382 of member 360 may be swung relative to a main portion 384 of the member 360, to imitate the motion of the human head. To that end, member 360 is provided with a joint or articulation 386 connecting segment 382 and main portion 384 to one another. A plurality of tension cables 388a and 388b connected at a distal end to segment 382 and at a proximal end to an actuator 390 serve to pivot segment 382 relative to main portion 384 in response to manipulations of an operator.

As depicted in FIG. 312D, bar 358 may be brought into a locking engagement with trocar sleeve 380 to form a T-square configuration to stabilize bar 358 during a delicate procedure.

Figure 13:
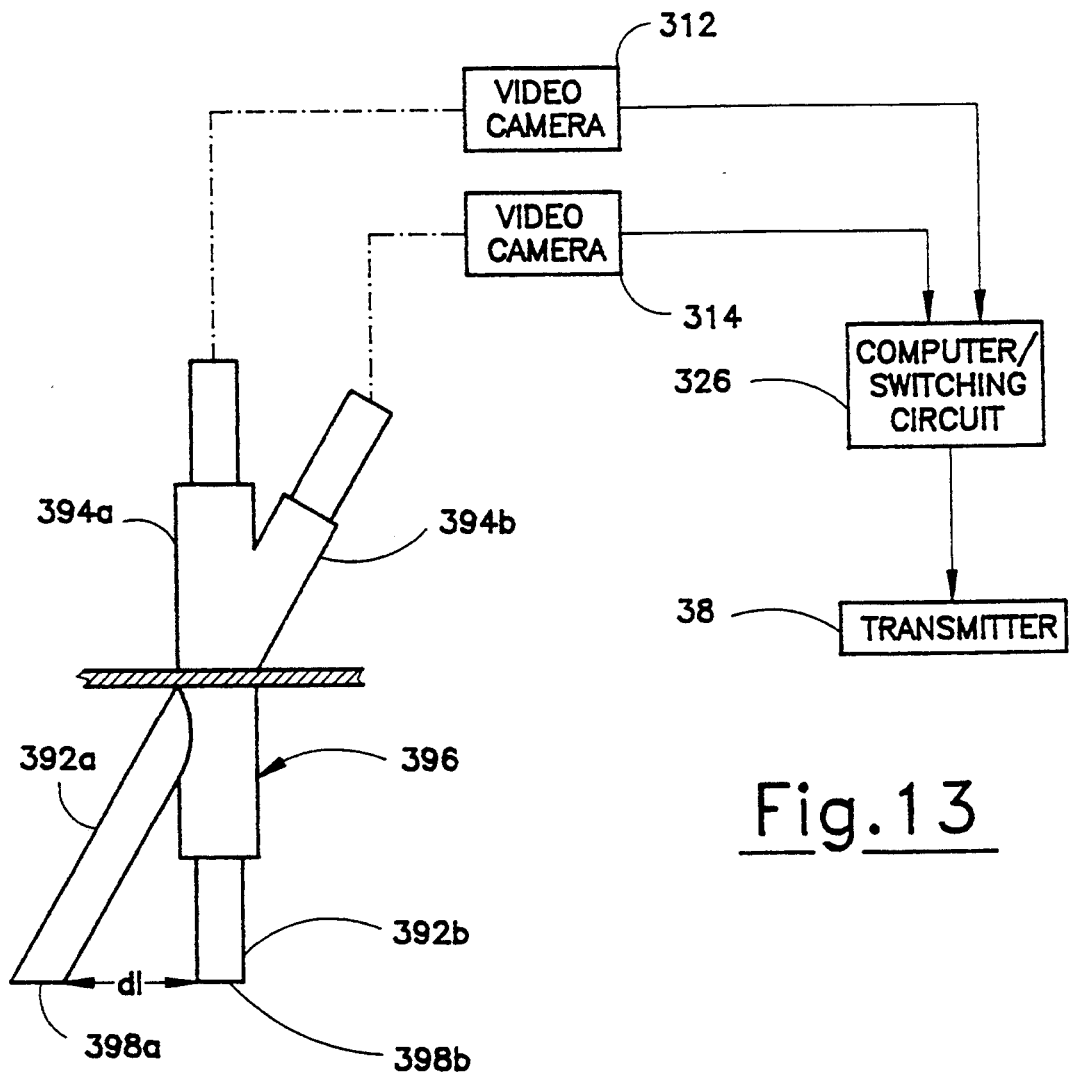
FIG. 13 is partially a block diagram and partially a schematic side elevational view of yet another specific embodiment of the stereoscopic laparoscope assembly of FIG. 1, showing a pair of laparoscopic instruments inserted through respective angled instrument channels of a trocar sleeve.

FIGS. 13 illustrates yet another specific embodiment of the stereoscopic laparoscope system of FIG. 9. A pair of rodlike laparoscopes 392a and 392b are inserted at an acute angle to one another along respective instrument insertion channels or paths defined by inlet tube sections 394a and 394b of a Y-port laparoscopic trocar sleeve 396. Such a sleeve is disclosed in U.S. Pat. No. 5,183,471 to Wilk. That patent is hereby incorporated by reference herein. The distal ends 398a and 398b of laparoscopes 392a and 392b are controllably disposable at distance d1 from one another.

Although the invention has been described in terms of particular embodiments and applications, one of ordinary skill in the art, in light of this teaching, can generate additional embodiments and modifications without departing from the spirit of or exceeding the scope of the claimed invention. For example, the spacing of the optical input elements may be maintained by a balloon disposed between the prongs of a steroscopic laparoscope in accordance with the present invention. The balloon is in a collapsed configuration during insertion of the pronged laparoscope through a trocar sleeve. Upon ejection of the prongs from the sleeve, the balloon is inflated to separate the prongs from one another. To that end, the prongs may be provided with an inherent spring bias tending to draw the prongs together, i.e., to maintain the prongs in a straightened configuration. The degree of inflation of the balloon determines the distances between the optical input elements at the distal ends of the prongs.

In another possible embodiment of the invention, the distance between the optical input elements is adjustable by a rack and pinion mechanism. Each optical input element (lens, optical fiber bundle input, or CCD, etc.) is mounted to a respective rack member.

Accordingly, it is to be understood that the drawings and descriptions herein are proferred by way of example to facilitate comprehension of the invention and should not be construed to limit the scope thereof.

What is claimed is:

1. A surgical method, comprising the steps of:
   providing an endoscopic instrument assembly with a flexible insertion member, said endoscopic instrument assembly having a plurality of biopsy channels extending parallel to said insertion member;
   also providing a plurality of flexible endoscopic tools having distal end portions;
   inserting said insertion member into a patient's body;
   obtaining a video image of internal body tissues inside said patient's body via said endoscopic instrument assembly;

transmitting, over an electromagnetic signaling link, a video signal encoding said video image to a remote location beyond a range of direct manual contact with said patient's body and said endoscopic instrument;

receiving actuator control signals from said remote location via said electromagnetic signaling link;

automatically inserting distal end portions of said tools into the patient's body via respective ones of said biopsy channels in response to the received actuator control signals; and automatically operating said tools in response to the received actuator control signals to effect a surgical operation on said internal body tissues.

2. The method defined in claim 1 wherein said endoscopic instrument assembly includes a pair of image transmission guides, said video signal including stereoscopic information from said image transmission guides, further comprising the step of providing stereoscopic visual information to a surgeon at said remote location.

3. The method defined in claim 2 wherein said step of providing stereoscopic visual information to a surgeon at said remote location includes the step of generating a single video image having staggered image components of different colors, filters over different eyes of a viewer serving to select between said staggered image components.

4. The method defined in claim 2 wherein said step of providing stereoscopic visual information to a surgeon at said remote location includes the steps of:
   providing two video monitors attached to one another for mounting to a person's head; and
   generating on said monitors two video images having staggered image components.

5. The method defined in claim 1 wherein said endoscopic instrument assembly includes a pair of image transmission guides, further comprising the step of transmitting images of two different views of said internal tissues along said image transmission guides, said video signal including stereoscopic information from said image transmission guides, further comprising the step of providing stereoscopic visual information to a surgeon at said remote location.

6. The method defined in claim 1, further comprising the step of automatically bending said distal end portions of said tools said tools in response to the received actuator control signals.

7. A surgical system comprising:
   an endoscopic instrument;
   camera means attached to said endoscopic instrument for obtaining video images of internal body tissues inside a patient's body via said endoscopic instrument;
   transmission means operatively connected to said camera means for transmitting, over an electromagnetic signaling link to a remote location beyond a range of direct manual contact with said patient's body and said endoscopic instrument, a video signal encoding said video image;
   receiver means for receiving actuator control signals from said remote location via said electromagnetic signaling link;
   a surgical instrument insertable into the patient's body and movable relative to the patient's body and said endoscopic instrument, said surgical instrument having a replaceable operative tip;
   robot actuator means operatively connected to said surgical instrument and said receiver means for actuating said surgical instrument in response to the actuator control signals received by said receiver means from said remote location; and
   robot selector means operatively connected to said surgical instrument and said receiver means for removing said operative tip and replacing said operative tip with a different operating tip in response to the actuator control signals received by said receiver means from said remote location.

8. The system recited in claim 7, further comprising means for automatically operating said endoscopic instrument in response to additional signals received by said receiver means from said remote location via said telecommunications link.

9. The system recited in claim 8 wherein said means for automatically operating said endoscopic instrument includes means for automatically operating said endoscopic instrument to vary said video image.

10. The system recited in claim 9 wherein said means for automatically operating said endoscopic instrument includes means for mechanically moving said endoscopic instrument with respect to the patient's body, thereby varying said video image.

11. The system defined in claim 7 wherein said robot actuator means is separate from said robot selector means.

12. The system defined in claim 7, further comprising additional camera means disposed permanently outside the patient and operatively connected to said transmission means for transmitting to said remote location a video image of a tool array disposed proximately to the patient.

13. The system defined in claim 7 wherein said camera means includes means for obtaining stereoscopic images of said internal body tissues.

14. The system defined in claim 7 wherein said robot actuator means includes means for operating said operative tip in response to the actuator control signals received by said receiver means from said remote location, said robot actuator means further including means for shifting said surgical instrument relative to the patient's body and said endoscopic instrument in response to the actuator control signals received by said receiver means from said remote location.

15. A surgical system comprising:
   an endoscopic instrument;
   camera means connected to said endoscopic instrument for obtaining stereoscopic video images of internal body tissues inside a patient's body via said endoscopic instrument;
   transmission means operatively connected to said camera means for transmitting, over an electromagnetic signaling link to a remote location beyond a range of direct manual contact with said patient's body and said endoscopic instrument, a video signal encoding said video images;
   receiver means for receiving actuator control signals from said remote location via said electromagnetic signaling link;
   a surgical instrument insertable into the patient's body and movable relative to the patient's body and said endoscopic instrument; and
   robot actuator means operatively connected to said surgical instrument and said receiver means for actuating said surgical instrument in response to the actuator control signals received by said receiver means from said remote location.

16. The system defined in claim 15 wherein said camera means includes:
a first video camera and a second video camera;
first optical means including a first optical input for receiving light reflected from said internal body tissues of the patient during a surgical procedure, said first optical means being operatively connected to said first camera for focusing a first image of said internal body tissues on photoreceptive componentry of said first camera;
second optical means including a second optical input for receiving light reflected from said internal body tissues during said surgical procedure, said second optical means being operatively connected to said second camera for focusing a second image of said internal body tissues on photoreceptive componentry of said second camera; and
spacer means operatively connected to said first and said second optical means for maintaining said first input and said second input spaced from one another inside the patient during said surgical procedure.

17. The system defined in claim 16, further comprising an elongate rigid member provided at a distal end with a pair of prongs, said spacer means including said prongs, said first optical input and said second optical input being disposed at distal ends of respective ones of said prongs, also comprising means operatively connected to said prongs for shifting said prongs away from one another upon an insertion of said elongate rigid member through a laparoscopic trocar sleeve traversing a skin surface of a patient.

18. The system defined in claim 16 wherein said spacer means includes a laparoscopic trocar sleeve having two instrument insertion channels oriented at an acute angle relative to one another, further comprising two elongate rods, said first optical input and said second optical input being disposed at distal ends of respective ones of said rods, said rods being inserted through respective ones of said instrument insertion channels.

19. The system defined in claim 16, further comprising a first elongate rigid member, said spacer means including a second elongate rigid member pivotably connected to a distal end of said first elongate rigid member, said first optical input and said second optical input being disposed at opposite ends of said second elongate member, also comprising means operatively connected to said second elongate rigid member for pivoting said second elongate rigid member relative to said first elongate rigid member, whereby said second elongate rigid member can be pivoted from an insertion configuration parallel to said first elongate rigid member to a use configuration at a predetermined angle with respect to said first elongate rigid member.

20. The system defined in claim 16 wherein said spacer means includes means for adjusting a spacing between said first and said second optical means.

* * * * *

UNITED STATES PATENT AND TRADEMARK OFFICE
Certificate

Patent No. 5,368,015                                        Patented: November 29, 1994

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Peter J. Wilk, New York, NY; and Robert Neil Sudol, Scarsda.

Signed and Sealed this Second Day of September 2003.

NICHOLAS D. LUCCHESI
*Supervisory Patent Examiner*
Art Unit 3764